United States Patent
Yokoi et al.

(10) Patent No.: US 8,648,065 B2
(45) Date of Patent: Feb. 11, 2014

(54) ANTIBACTERIAL MEDICINAL COMPOSITION OF ENHANCED ORAL ABSORPTIVITY

(75) Inventors: Yukiko Yokoi, Yokohama (JP); Shigeru Chikase, Yokohama (JP); Hiroyuki Yamaguchi, Osaka (JP)

(73) Assignee: Meiji Seika Pharma Co., Ltd., Tokyo-To (JP)

( * ) Notice: Subject to any disclaimer, the term of this patent is extended or adjusted under 35 U.S.C. 154(b) by 1605 days.

(21) Appl. No.: 10/530,046

(22) PCT Filed: Apr. 28, 2003

(86) PCT No.: PCT/JP03/05461

§ 371 (c)(1),
(2), (4) Date: Apr. 1, 2005

(87) PCT Pub. No.: WO2004/030673

PCT Pub. Date: Apr. 15, 2004

(65) Prior Publication Data

US 2006/0051411 A1  Mar. 9, 2006

(30) Foreign Application Priority Data

Oct. 2, 2002 (JP) .................................. 2002-290367

(51) Int. Cl.
*A61K 31/545* (2006.01)
*A01N 43/04* (2006.01)
*A61K 31/715* (2006.01)
*A61K 31/70* (2006.01)

(52) U.S. Cl.
USPC ................. 514/200; 514/57; 514/23

(58) Field of Classification Search
USPC ............................................. 514/200, 57, 23
See application file for complete search history.

(56) References Cited

U.S. PATENT DOCUMENTS

| | | | |
|---|---|---|---|
| 4,470,980 A | 9/1984 | Higuchi et al. | |
| 5,948,422 A | 9/1999 | van Koutrik et al. | |
| 5,958,915 A | 9/1999 | Abe et al. | |
| 6,294,669 B1 | 9/2001 | Yasui et al. | |
| 6,342,493 B1 | 1/2002 | Onodera et al. | |
| 6,441,162 B2 | 8/2002 | Yasui et al. | |
| 6,486,149 B2 | 11/2002 | Onodera et al. | |
| 2002/0015730 A1* | 2/2002 | Hoffmann et al. ............. | 424/470 |
| 2004/0115272 A1* | 6/2004 | Ohta ............................... | 424/486 |

FOREIGN PATENT DOCUMENTS

| | | | |
|---|---|---|---|
| EP | 0 339 465 | 11/1989 | |
| JP | 60-126230 | 7/1985 | |
| JP | 60-132918 | 7/1985 | |
| JP | 60-188230 | 7/1985 | |
| JP | 60-188320 | 9/1985 | |
| JP | 62-265226 | 11/1987 | |
| JP | 1-128926 | 5/1989 | |
| JP | 11-092780 | 4/1999 | |
| JP | 2001-131071 | 5/2001 | |
| JP | 02/087588 | 11/2002 | |
| WO | 97/13516 | 4/1997 | |
| WO | 99/34832 | 7/1999 | |
| WO | WO0006126 | * 2/2000 | ............... A61K 9/20 |
| WO | 02/087588 | 11/2002 | |
| WO | 02/096354 | 12/2002 | |
| WO | 2009/098963 | 8/2009 | |

OTHER PUBLICATIONS

Product Information sheet for Tween 80 found in Sigma-Aldrich catalog at http://www.sigmaaldrich.com; 2 pages describing chemical properties of sorbitan monooleate.*
Nakamura, Shingo. Foods and Food Ingredients Journal of Japan, 1999, vol. 180, p. 1.*
Bujan et al. Langmuir 2001, vol. 17, pp. 6461-6470.*
Herrera et al. JAOCS, 1996, vol. 73, No. 3, pp. 321-326.*
Nakamura et al. Food and Food ingredient Journal of Japan, 1999, vol. 180, pp. 2-29, English Translated Version.*
Y. Yokoi et al., "Effects of Sugar Ester and Hydroxypropyl Methylcellulose on the Physicochemical Stability of Amorphous Cefditoren Pivoxil in Aqueous Suspension", International Journal of Pharmaceutics, vol. 290, No. 1-2, Feb. 16, 2005, pp. 91-99.
Yokoi, Yukiko, et al., "Effects of sugar ester and hydroxypropyl methylcellulose on the physicochemical stability of amorphous cefditoren pivoxil in aqueous suspension", International Journal of Pharmaceuticals, 290 (2005), pp. 91-99.

* cited by examiner

*Primary Examiner* — Samira Jean-Louis
(74) *Attorney, Agent, or Firm* — Wenderoth, Lind & Ponack, L.L.P.

(57) ABSTRACT

An objective of the present invention is to provide a cefditoren pivoxil pharmaceutical preparation which can safely be administered to a patient and not only improves wettability of cefditoren pivoxil, but also further improves absorbability through the intestinal tracts by maintaining amorphous particles having a high oral absorbability in a liquid for a long period of time. The present invention is a pharmaceutical composition comprising amorphous cefditoren pivoxil and a sucrose fatty acid ester, which is obtainable by mixing or wet-granulating particles containing amorphous cefditoren pivoxil with the sucrose fatty acid ester while amorphous cefditoren pivoxil maintains its particle state.

23 Claims, 1 Drawing Sheet

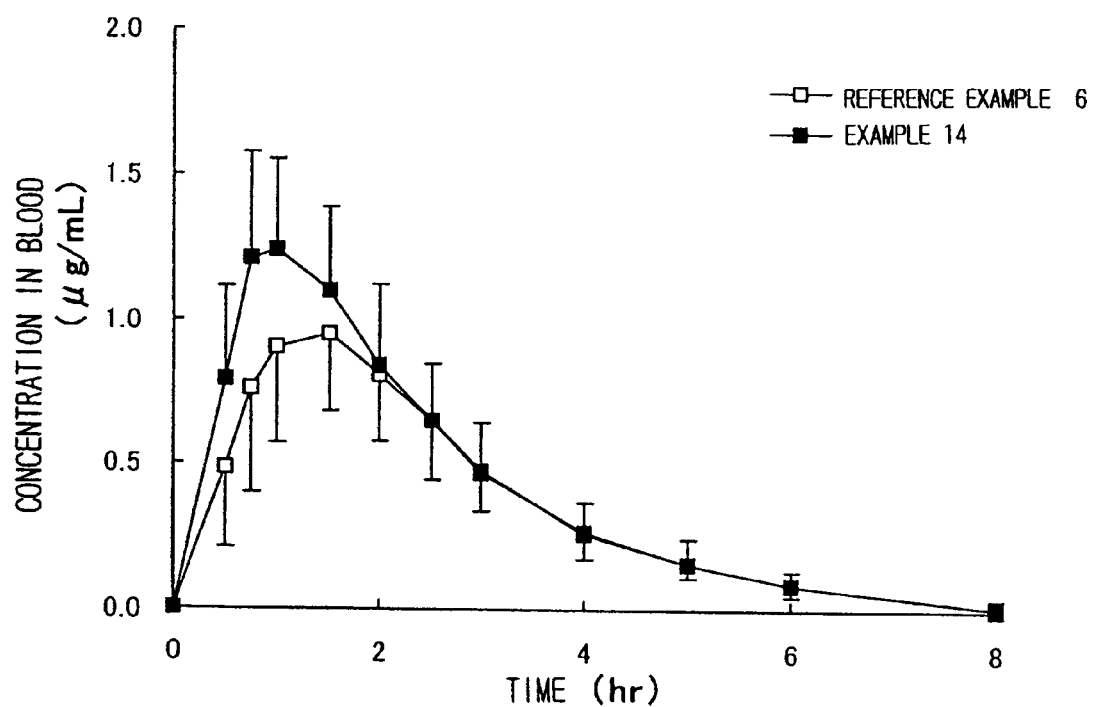

ANTIBACTERIAL MEDICINAL COMPOSITION OF ENHANCED ORAL ABSORPTIVITY

BACKGROUND OF THE INVENTION

1. Field of the Invention

The present invention relates to antibiotic pharmaceutical compositions with improved oral absorbability, more specifically to antibiotic pharmaceutical compositions comprising amorphous cefditoren pivoxil.

2. Background Art

An antibiotic compound cefditoren is a cephem compound represented by formula (A):

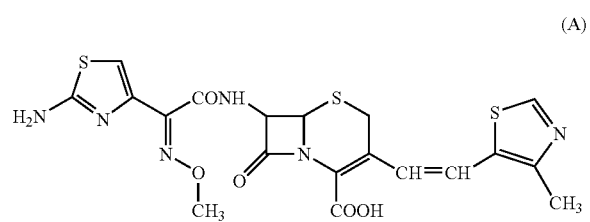

Its chemical name is (+)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylic acid. This compound is described in Japanese Patent Publication No. 64503/1991 under the chemical name of 7-[2-methoxyimino-2-(2-aminothiazol-4-yl)acetamido]-3-[2-(4-methylthiazol-5-yl)vinyl]-3-cephem-4-carboxylic acid (syn-isomer, cis-isomer).

A pivaloyloxymethyl ester of cefditoren, in which a carboxylic acid group on position 2 of the cephem compound is esterified with a pivaloyloxymethyl group for the purpose of improving its absorbability through the digestive tracts upon oral administration (hereinafter referred to as "oral absorbability"), is called cefditoren pivoxil. This prodrug compound is represented by formula (B):

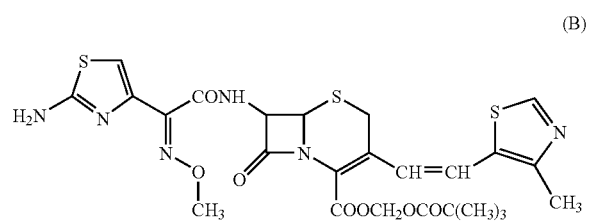

and its chemical name is (−)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylic acid 2,2-dimethylpropionyloxymethyl ester. This ester compound is generally considered to exhibit high oral absorbability as compared to the original acid-form drug. However, the esterification of cefditoren has not necessarily resulted in enhancement or improvement of the oral absorbability to the satisfactory level.

In order to improve the oral absorbability of cefditoren pivoxil, a pharmaceutical preparation in which cyclodextrin or hydroxypropyl cellulose that is a water-soluble polymer cellulose derivative is added to cefditoren pivoxil has been proposed (Japanese Patent Publication No. 78234/1994 and Japanese Patent Laid-Open Publication No. 17866/1995). However, the addition of cyclodextrin to cefditoren pivoxil extremely intensified the bitterness derived from cefditoren pivoxil and pharmaceutical tablets or granules obtained with the addition of hydroxypropyl cellulose became bulky, which made oral administration difficult.

In order to solve these problems, a pharmaceutical preparation in which a water-soluble caseinate is added to cefditoren pivoxil has recently been proposed (Japanese Patent No. 2831135). However, this preparation could not be administered to a patient suffering from a milk allergy since casein is a protein derived from milk.

Thus, a pharmaceutical preparation wherein cefditoren pivoxil can be safely administered to a patient and oral absorbability sufficient enough to exert its expected pharmaceutical effect is secured has been in demand.

On the other hand, as a means to improve oral absorbability of a poorly soluble drug, a solid composition which is obtained by amorphousizing the poorly soluble drug in the presence of a polymer base and a nonionic surfactant is disclosed in WO 96/19239. It is disclosed that the above-mentioned composition maintains its amorphousness state when dispersed in a liquid and that the maximum concentration in the blood (Cmax) and the area under the curve of blood concentration (AUC) increase when orally administered to dogs, that is, the oral absorbability can be improved. However, shortening of the time required to reach the maximum blood concentration, which is an index of immediate effect, has not been achieved. Further, the disclosed solid composition is notably characterized in that the drug, the polymer base, and the nonionic surfactant are mixed in a molecular state, namely in a state of solid dispersion composition. Furthermore, such a pharmaceutical preparation is produced using a spray drying method in which a solvent such as dichloromethane is occasionally used, which requires a concern for environment and a security for safety.

Further, Japanese Patent No. 3290970 discloses, as a means to improve oral absorbability of a poorly soluble drug, a solid pharmaceutical preparation containing poorly soluble NSAIDs, a water-soluble polymer base and a nonionic surfactant, which is characterized in that the poorly soluble NSAIDs are in a crystalline state.

Further, WO 99/34832 discloses a composition comprising a crystallographically stable, amorphous cephalosporin and a process for the preparation thereof, indicating that the oral absorbability can be improved by amorphousizing the cephalosporin. Japanese Patent Laid-Open Publication No. 131071/2001 discloses a process for the preparation of amorphous cefditoren pivoxil, in which the oral absorbability can be improved by amorphousizing cefditoren pivoxil. Further, WO 02/87588 discloses a process for producing an amorphous composition, in which an organic polymer is mixed with cefditoren pivoxil crystals and the obtained mixture is ground.

SUMMARY OF THE INVENTION

However, the present inventors confirmed that a suspension in which crystals of cefditoren pivoxil were sufficiently suspended exhibited extremely low oral absorbability in dogs as compared to an amorphous suspension. In other words, it was found that the process disclosed in Japanese Patent No. 3290970 was not practically applicable to cefditoren pivoxil. On the other hand, since amorphous cefditoren pivoxil is apt to change into a crystalline state in a solution, an antibiotic pharmaceutical composition comprising amorphous cefditoren pivoxil still needs to be improved.

The present inventors have now found that crystallization of amorphous cefditoren pivoxil was inhibited by simply mixing amorphous cefditoren pivoxil with a sucrose fatty acid ester. The present inventors also confirmed that a solid composition comprising a physical mixture of amorphous cefditoren pivoxil and a sucrose fatty acid ester was excellent in its absorbability and immediate effect. This finding was surprising because, upon formulating amorphousized drugs into pharmaceutical preparations, a pharmaceutical preparation obtained by simply mixing active ingredients was known to be insufficient for its absorbability and immediate effect as compared to a solid dispersion compound or a soluble complex with cyclodextrin or the like.

Thus, an objective of the present invention is to provide a cefditoren pivoxil pharmaceutical preparation which can safely be administered to a patient and not only improves wettability of cefditoren pivoxil, but also further improves absorbability through the intestinal tracts by maintaining amorphous particles having high oral absorbability in a liquid for a long period of time.

According to the present invention, there is provided a pharmaceutical composition comprising amorphous cefditoren pivoxil and a sucrose fatty acid ester, which is obtainable by mixing or wet-granulating particles containing amorphous cefditoren pivoxil with the sucrose fatty acid ester while amorphous cefditoren pivoxil maintains its particle state.

The pharmaceutical composition according to the present invention is advantageous in that the amorphous state of amorphous cefditoren pivoxil can be maintained for a long period of time and that the oral absorbability and the immediate effect of cefditoren pivoxil are excellent.

Further, the pharmaceutical composition according to the present invention is expected to have high dispersibility and elutability in an aqueous solution because of its excellent wettability. The pharmaceutical composition according to the present invention is advantageous in that its production process is simple and does not cause any safety or environmental problem because it can be produced by simply mixing particles containing amorphous cefditoren pivoxil and a sucrose fatty acid ester or the like without use of any solvent in the formulation process.

BRIEF DESCRIPTION OF THE DRAWING

FIG. 1 shows the change with time in blood cefditoren concentrations (n=24, average±S.D.) when the pharmaceutical composition according to the present invention (Example 14) and the composition of Reference Example 6 were orally administered to healthy adults.

DETAILED DESCRIPTION OF THE INVENTION

In the pharmaceutical composition according to the present invention, amorphous cefditoren pivoxil is present in the interior of particles and a sucrose fatty acid ester is present in the exterior of the same particles. Examples of such particles include particles essentially consisting of amorphous cefditoren pivoxil and particles composed of a mixture of amorphous cefditoren pivoxil and one or more pharmaceutically acceptable additives (for example, water-soluble polymers) other than sucrose fatty acid esters.

Particles containing amorphous cefditoren pivoxil to be used can be commercially available products or may be produced according to a known method. The particles essentially consisting of amorphous cefditoren pivoxil can be produced according to the method described in Japanese Patent Publication No. 64503/1991. The particles essentially consisting of amorphous cefditoren pivoxil can also be produced, for example, by precipitating a cefditoren pivoxil solution with an organic solvent having low solubility, by precipitating a cefditoren pivoxil solution in ethyl acetate with isopropyl ether, by spray-drying a cefditoren pivoxil solution, by lyophilizing a cefditoren pivoxil solution, or by grinding crystalline cefditoren pivoxil. Such particles can be produced in accordance with Japanese Patent Laid-Open Publication No. 131071/2001. Particles composed of a homogenous mixture of amorphous cefditoren pivoxil and a water-soluble polymer can be produced, for example, by co-precipitating cefditoren pivoxil and the water-soluble polymer. Such particles can be produced in accordance with WO 99/34832.

A sucrose fatty acid ester added to the pharmaceutical composition according to the present invention can be used by selecting from commercially available products.

The sucrose fatty acid ester can be, not particularly limited to, any ester which is pharmaceutically acceptable and extends the amorphousness-maintaining period for amorphous cefditoren pivoxil. A hydrophilic ester having a high HLB value is preferred and, for example, one with an HLB value of more than 10, preferably 11 to 20, can be used. The HLB value can be calculated in accordance with "Standard Methods for Analysis of Fats and Oil" (1971) edited by Japan Oil Chemist's Society. The sucrose fatty acid ester can be used singly or as a mixture of two or more kinds thereof, if necessary.

The amount of the sucrose fatty acid ester to be added can be 0.1 to 100 mg, preferably 0.1 to 5 mg, on the basis of an amount equivalent to 100 mg potency of cefditoren pivoxil.

Preferably, the pharmaceutical composition according to the present invention can further contain a pharmaceutically acceptable polymer. The amorphousness-maintaining period for amorphous cefditoren pivoxil can be markedly extended by adding a pharmaceutically acceptable polymer to particles containing amorphous cefditoren pivoxil together with a sucrose fatty acid ester.

The pharmaceutically acceptable polymer to be added to the pharmaceutical composition according to the present invention can be used by selecting from commercially available products.

The polymer can be, not particularly limited to, any polymer which does not inhibit the extension of the amorphousness-maintaining period for amorphous cefditoren pivoxil or further extends the amorphousness-maintaining period. A pharmaceutically acceptable water-soluble polymer can be preferably used.

Examples of the polymers usable include hydroxypropylmethyl cellulose (HPMC), methylcellulose (MC), hydroxyethyl cellulose (HEC), polyvinylpyrrolidone (PVP), and hydroxypropyl cellulose (HPC), and etc., preferably, HPMC, MC, and HEC. The polymer can be used singly or as a mixture of two or more kinds thereof, if necessary.

The amount of the polymer to be added to particles containing amorphous cefditoren pivoxil can be 1 to 100 mg, preferably 1 to 50 mg, on the basis of an amount equivalent to 100 mg potency of cefditoren pivoxil.

The pharmaceutical composition according to the present invention is characterized in that it is a mixture or a wet-granulated product in which powders or particles containing amorphous cefditoren pivoxil are present in a sucrose fatty acid ester and, optionally, a pharmaceutically acceptable polymer, and/or one or more pharmaceutically acceptable additives, while the amorphous particles are maintained. Namely, the pharmaceutical composition according to the present invention is distinctly different from a mixture wherein an active ingredient is dispersed in other ingredients including a sucrose fatty acid ester at a molecular level, for example, a solid dispersion composition which is obtained by dissolving an active ingredient and other components including a sucrose fatty acid ester in a solvent and then removing the solvent by distillation. The pharmaceutical composition according to the present invention can be produced, for example, by (1) mixing all kinds of ingredients in a powder or granular form as they are, (2) mixing all kinds of ingredients in a solid form while pulverizing, or (3) adding a binding solution, which is obtained by dissolving a binding agent or like other than an active ingredient in a solvent (for example, purified water), to a powder mixture containing the active ingredient and wet-granulating the obtained mixture.

The pharmaceutical composition according to the present invention can be formulated into various dosage forms as a pharmaceutical preparation suitable for oral administration. Examples of the pharmaceutical preparations suitable for oral administration include powders, fine granules, granules, tablets, and capsules. The pharmaceutical preparation suitable for oral administration can be produced by an ordinary method using one or more pharmaceutically acceptable additives to be used ordinarily, such as excipients, fillers, binding agents, wetting agents, disintegrants, surfactants, lubricants, dispersing agents, buffering agents, preservatives, solution adjuvants, antiseptics, flavoring agents, analgesic agents, and stabilizers.

The amount of cefditoren pivoxil in the pharmaceutical composition varies depending on its dosage form. It can be 5 to 90% by weight, preferably 10 to 80% by weight, of the entire composition. The amount of administration for the treatment and prevention of bacterial infection or the like can be appropriately determined by considering the usage, the age and gender of the patient, the severity of the symptoms and the like. An appropriate dose for an adult can be about 300 to 800 mg per day, which can be administered daily as a single or divided dose.

EXAMPLES

The present invention will be further illustrated in detail by the following examples that are not intended to restrict the scope of the present invention.

Reference Examples 1 to 5 and Examples 1 to 5

Homogenous powder mixtures were obtained by mixing particles containing amorphous cefditoren pivoxil and surfactants at the formulation ratios shown in Table 1.

The particles containing amorphous cefditoren pivoxil used in the examples were prepared by co-precipitating cefditoren pivoxil and a water-soluble polymer in accordance with WO 99/34832.

TABLE 1

| | Surfactant | Formulation ratio (drug:surfactant) |
|---|---|---|
| Reference Example 1 | — | 100 mg potency:— |
| Example 1 | Sucrose fatty acid ester (DK Ester SS, HLB value = 20, Daiichi Kogyo Seiyaku Co., Ltd.) | 100 mg potency:5 mg |
| Example 2 | Sucrose fatty acid ester (DK Ester F-140, HLB value = 13, Daiichi Kogyo Seiyaku Co., Ltd.) | 100 mg potency:5 mg |
| Example 3 | Sucrose fatty acid ester (DK Ester F-110, HLB value = 11, Daiichi Kogyo Seiyaku Co., Ltd.) | 100 mg potency:5 mg |

TABLE 1-continued

| | Surfactant | Formulation ratio (drug:surfactant) |
|---|---|---|
| Example 4 | Sucrose fatty acid ester (Surfhope J-1811, HLB value = 11, Mitsubishi Kagaku Foods Corporation) | 100 mg potency:5 mg |
| Example 5 | Sucrose fatty acid ester (Surfhope J-1216, HLB value = 16, Mitsubishi Kagaku Foods Corporation) | 100 mg potency:5 mg |
| Reference Example 2 | Polysorvate 80 (Nikkol TO-10M, Nikko Chemicals Co., Ltd.) | 100 mg potency:5 mg |
| Reference Example 3 | Polyoxyl 40 (Nikkol MYS-40, Nikko Chemicals Co., Ltd.) | 100 mg potency:5 mg |
| Reference Example 4 | POE (105) POP (5) glycol (PEP-101, Freund Industrial Co., Ltd.) | 100 mg potency:5 mg |
| Reference Example 5 | Sodium lauryl sulfate (Emal OS, Kao Corporation) | 100 mg potency:5 mg |

Test Example 1

Suspensions were prepared such that the concentration of amorphous cefditoren pivoxil in the suspensions was 10 mg/ml and individual additives were added to the suspensions at the formulation ratios shown in Table 1. More specifically, 350 ml of water or 350 ml of an aqueous solution of individual surfactant was added to amorphous cefditoren pivoxil on the basis of an amount equivalent to 3.5 g potency thereof to obtain each of the suspensions. The amorphousness-maintaining period was evaluated for the suspensions thus prepared.

The amorphousness-maintaining period was measured as follows. Specifically, the suspensions were stored at 25° C. under air-tight conditions and sampled immediately, 1 day, 2 days, 3 days, 5 days, 7 days, 10 days, and 14 days after the preparation. The sampled suspensions were centrifuged and the resultant residues were dried under reduced pressure and subjected to the power X-ray diffraction analysis. The results are shown in Table 2.

TABLE 2

| | Immediately after the preparation | 1 D | 2 D | 3 D | 5 D | 7 D | 10 D | 14 D |
|---|---|---|---|---|---|---|---|---|
| Reference Example 1 | A | A | C | C | C | C | C | C |
| Example 1 | A | A | A | A | C | C | C | C |
| Example 2 | A | A | A | C | C | C | C | C |
| Example 3 | A | A | A | C | C | C | C | C |
| Example 4 | A | A | A | C | C | C | C | C |
| Example 5 | A | A | A | C | C | C | C | C |
| Reference Example 2 | C | C | C | C | C | C | C | C |
| Reference Example 3 | C | C | C | C | C | C | C | C |
| Reference Example 4 | A | C | C | C | C | C | C | C |
| Reference Example 5 | A | A | C | C | C | C | C | C |

C: Crystalline
A: Amorphous

Crystallization of amorphous cefditoren pivoxil was stimulated with the surfactants other than sucrose fatty acid esters, while the amorphousness-maintaining period was extended with sucrose fatty acid esters.

Examples 6 to 13

Homogenous powder mixtures were obtained by mixing particles containing amorphous cefditoren pivoxil, surfactants, and polymers at the formulation ratios shown in Table 3.

TABLE 3

|  | Surfactant | Polymer | Formulation ratio (drug:surfactant:polymer) |
|---|---|---|---|
| Example 6 | Sucrose fatty acid ester | — | 100 mg potency:0.1 mg:— |
| Example 7 | Sucrose fatty acid ester | HPMC | 100 mg potency:0.1 mg:1 mg |
| Example 8 | Sucrose fatty acid ester | HPMC | 100 mg potency:0.1 mg:100 mg |
| Example 9 | Sucrose fatty acid ester | HPMC | 100 mg potency:5 mg:1 mg |
| Example 10 | Sucrose fatty acid ester | HPMC | 100 mg potency:5 mg:50 mg |
| Example 11 | Sucrose fatty acid ester | MC | 100 mg potency:5 mg:50 mg |
| Example 12 | Sucrose fatty acid ester | HEC | 100 mg potency:5 mg:50 mg |
| Example 13 | Sucrose fatty acid ester | — | 100 mg potency:100 mg:— |

Sucrose fatty acid ester: DK Ester SS, HLB value = 20, Daiichi Kogyo Seiyaku Co., Ltd.
HPMC (hydroxypropylmethyl cellulose): TC-5R, Shin-Etsu Chemical Co., Ltd.
MC (methylcellulose): Metholose SH-4, Shin-Etsu Chemical Co., Ltd.
HEC (hydroxyethyl cellulose): HEC Daicel SP400, Daicel Chemical Industries, Ltd.

Test Example 2

Suspensions were prepared such that the concentration of the amorphous cefditoren pivoxil in the suspensions was 10 mg/ml and individual additives were added to the suspensions at the formulation ratios shown in Table 3. More specifically, a sucrose fatty acid ester (DK Ester SS) and individual polymer were dissolved into 350 ml of water and the resultant aqueous solution was added to amorphous cefditoren pivoxil on the basis of an amount equivalent to 3.5 g potency thereof to obtain each of the suspensions. The amorphousness-maintaining period was evaluated for the suspensions thus prepared.

The amorphousness-maintaining period was measured as follows. Specifically, the suspensions were stored at 25° C. under air-tight conditions and sampled immediately, 1 day, 2 days, 3 days, 5 days, 7 days, 10 days, and 14 days after the preparation. The sampled suspensions were centrifuged and the resultant residues were dried under reduced pressure and subjected to the power X-ray diffraction analysis. The results are shown in Table 4.

TABLE 4

|  | Sucrose fatty acid ester mixed* | Polymer mixed* | Immediately after the preparation | 1 D | 2 D | 3 D | 5 D | 7 D | 10 D | 14 D |
|---|---|---|---|---|---|---|---|---|---|---|
| Reference Example 1 | — | — | A | A | C | C | C | C | C | C |
| Example 6 | 0.1 mg | — | A | A | A | C | C | C | C | C |
| Example 7 | 0.1 mg | HPMC 1 mg | A | A | A | C | C | C | C | C |
| Example 8 | 0.1 mg | HPMC 100 mg | A | A | A | A | C | C | C | C |
| Example 1 | 5 mg | — | A | A | A | A | C | C | C | C |
| Example 9 | 5 mg | HPMC 1 mg | A | A | A | A | C | C | C | C |
| Example 10 | 5 mg | HPMC 50 mg | A | A | A | A | A | A | A | C |
| Example 11 | 5 mg | MC 50 mg | A | A | A | A | A | A | C | C |
| Example 12 | 5 mg | HEC 50 mg | A | A | A | A | A | A | C | C |
| Example 13 | 100 mg | — | A | A | A | A | A | C | C | C |

C: Crystalline
A: Amorphous
*Formulated on the basis of an amount equivalent to 100 mg potency of amorphous cefditoren pivoxil.

The extension of the amorphousness-maintaining period was observed with the addition of only 0.1 mg of sucrose fatty acid esters. Furthermore, the further extension of the amorphousness-maintaining period was observed with the further addition of polymers.

Reference Examples 6 and 7 and Example 14

Tablets were prepared with the formulation ratios shown in Table 5. Binding solutions were obtained by dissolving a binding agent in Reference Example 6, hydroxypropylmethyl cellulose in Reference Example 7, and a sucrose fatty acid ester and hydroxypropylmethyl cellulose in Example 14, respectively, into purified water. Next, an appropriate amount of each of the above-mentioned binding solution was added to a powder mixture of the rest of the ingredients and the admixture was wet-granulated by an ordinary method. The purified water was then removed by distillation to obtain granules. The granules (200 mg) were compressed to obtain flat tablets.

TABLE 5

|  | Reference Example 6 | Reference Example 7 | Example 14 |
|---|---|---|---|
| Particles containing amorphous cefditoren pivoxil | equivalent to 100 mg potency | equivalent to 100 mg potency | equivalent to 100 mg potency |
| Sodium caseinate | 50 mg | — | — |
| Sucrose fatty acid ester | — | — | 5 mg |
| Hydroxypropylmethyl cellulose | — | 40 mg | 40 mg |
| Disintegrant | 30 mg | 30 mg | 30 mg |
| Binding agent | 20 mg | — | — |
| Excipient | Balance | Balance | Balance |
| Total | 1000 mg | 1000 mg | 1000 mg |

Test Example 3

Wettability was evaluated for the tablets obtained in Reference Examples 6 and 7, and Example 14. To the tablets obtained, 10 µl of water was added dropwise and the time required for the water drops to be completely absorbed into the tablets was measured. The results are shown in Table 6.

TABLE 6

|  | 1 | 2 | 3 | Average | S.D. |
|---|---|---|---|---|---|
| Reference Example 6 | 431 | 422 | 427 | 427 | 5 |
| Reference Example 7 | 745 | 584 | 648 | 659 | 81 |
| Example 14 | 289 | 155 | 233 | 226 | 67 |

(Unit: second)

The tablets containing sodium caseinate (Reference Example 6) exhibited faster water infiltration rates than the tablets without sodium caseinate and a sucrose fatty acid ester (Reference Example 7). Further, the tablets containing a sucrose fatty acid ester (Example 14) exhibited markedly faster water filtration rates than the tablets containing sodium caseinate. The composition according to the present invention was revealed to have markedly improved wettability as compared to those produced using conventional wettability-improving methods.

Test Example 4

The granules obtained in Reference Example 6 and Example 14 were evaluated for their oral absorbability in human. Specifically, a crossover test was carried out with 24 healthy adults. The granules (1000 mg) were orally administered with 150 ml of water under fasting conditions and the blood was sampled after given hours to measure the concentration in blood by HPLC. The results are shown in Tables 7 and 8 and FIG. 1.

TABLE 7

|  | Reference Example 6 | | Example 14 | |
|---|---|---|---|---|
| Time (hours) | Avg. conc. in blood | S.D. | Avg. conc. in blood | S.D. |
| 0.5 | 0.49 | 0.28 | 0.79 | 0.32 |
| 0.75 | 0.76 | 0.36 | 1.21 | 0.37 |
| 1 | 0.90 | 0.33 | 1.24 | 0.31 |
| 1.5 | 0.95 | 0.27 | 1.10 | 0.29 |
| 2 | 0.81 | 0.23 | 0.84 | 0.28 |
| 2.5 | 0.65 | 0.20 | 0.65 | 0.20 |
| 3 | 0.48 | 0.14 | 0.47 | 0.17 |
| 4 | 0.26 | 0.09 | 0.27 | 0.10 |
| 5 | 0.16 | 0.05 | 0.16 | 0.08 |
| 6 | 0.09 | 0.04 | 0.09 | 0.04 |
| 8 | 0.01 | 0.03 | 0.01 | 0.03 |

(Unit: μg/ml)

TABLE 8

|  | Max. conc. in blood (Cmax) (μg/ml) | | Area under curve of conc. in blood (AUC) (μg · hr/ml) | | Time to reach max. conc. in blood (Tmax) (hr) | |
|---|---|---|---|---|---|---|
|  | Average | S.D. | Average | S.D. | Average | S.D. |
| Ref. Example 6 | 1.07 | 0.28 | 2.85 | 0.66 | 1.46 | 0.48 |
| Example 14 | 1.30 | 0.33 | 3.30 | 0.90 | 0.96 | 0.28 |

As compared to the conventional granules with improved oral absorbability (Reference Example 6), the composition according to the present invention (Example 14) exhibited the increases in the maximum concentration in blood (Cmax) and the area under the curve of the concentration in the blood (AUC) and the reduction in time required to reach the maximum concentration in blood (Tmax), which shows that its oral absorbability and immediate effect are markedly improved.

The invention claimed is:

1. A pharmaceutical composition comprising amorphous cefditoren pivoxil and a sucrose fatty acid ester, which is obtainable by mixing or wet-granulating particles containing amorphous cefditoren pivoxil with the sucrose fatty acid ester while amorphous cefditoren pivoxil maintains its particle state, wherein crystallization of the amorphous cefditoren pivoxil is inhibited in aqueous medium for a period of at least two days.

2. The pharmaceutical composition according to claim 1, wherein the weight ratio of the sucrose fatty acid ester to the cefditoren pivoxil is in a range of from 0.0008 to 0.816.

3. The pharmaceutical composition according to claim 1, which further comprises a pharmaceutically acceptable polymer.

4. The pharmaceutical composition according to claim 3, wherein the polymer is one or more water-soluble high polymers selected from the group consisting of hydroxypropylmethyl cellulose, methylcellulose, hydroxyethyl cellulose, polyvinylpyrrolidone, and hydroxypropyl cellulose.

5. The pharmaceutical composition according to claim 3, wherein the weight ratio of the polymer to the cefditoren pivoxil is in a range of from 0.008 to 0.816.

6. The pharmaceutical composition according to claim 1, which further comprises one or more pharmaceutically acceptable additives.

7. The pharmaceutical composition according to claim 2, which further comprises a pharmaceutically acceptable polymer.

8. The pharmaceutical composition according to claim 7, wherein the polymer is one or more water-soluble high polymers selected from the group consisting of hydroxypropylmethyl cellulose, methylcellulose, hydroxyethyl cellulose, polyvinylpyrrolidone, and hydroxypropyl cellulose.

9. The pharmaceutical composition according to claim 4, wherein the weight ratio of the polymer to the cefditoren pivoxil is in a range of from 0.008 to 0.816.

10. The pharmaceutical composition according to claim 7, wherein the weight ratio of the polymer to the cefditoren pivoxil is in a range of from 0.008 to 0.816.

11. The pharmaceutical composition according to claim 8, wherein the weight ratio of the polymer to the cefditoren pivoxil is in a range of from 0.008 to 0.816.

12. The pharmaceutical composition according to claim 2, which further comprises one or more pharmaceutically acceptable additives.

13. The pharmaceutical composition according to claim 3, which further comprises one or more pharmaceutically acceptable additives.

14. The pharmaceutical composition according to claim 4, which further comprises one or more pharmaceutically acceptable additives.

15. The pharmaceutical composition according to claim 7, which further comprises one or more pharmaceutically acceptable additives.

16. The pharmaceutical composition according to claim 8, which further comprises one or more pharmaceutically acceptable additives.

17. The pharmaceutical composition according to claim 9, which further comprises one or more pharmaceutically acceptable additives.

18. The pharmaceutical composition according to claim 10, which further comprises one or more pharmaceutically acceptable additives.

19. The pharmaceutical composition according to claim 11, which further comprises one or more pharmaceutically acceptable additives.

20. The pharmaceutical composition according to claim 1, wherein the composition is free from polysorbate 80.

21. A pharmaceutical composition comprising amorphous cefditoren pivoxil and sucrose fatty acid ester, wherein the weight ratio of the sucrose fatty acid ester to the amorphous cefditoren pivoxil is in a range of from 0.0008 to 0.04, and wherein the composition is capable of retaining the amorphicity of said amorphous cefditoren pivoxil in aqueous medium for at least two days.

22. A pharmaceutical composition comprising amorphous cefditoren pivoxil in combination with an amount of sucrose fatty acid ester that is effective to maintain said amorphous cefditoren pivoxil in an amorphous state in aqueous medium for a period of at least two days.

23. The pharmaceutical composition according to claim 1, wherein the weight ratio of the sucrose fatty acid ester to the cefditoren pivoxil is in a range of from 0.0008 to 0.04.

* * * * *